(12) United States Patent
Delhomel et al.

(10) Patent No.: US 7,385,082 B2
(45) Date of Patent: Jun. 10, 2008

(54) PREPARATION OF 1,3-DIPHENYLPROP-2-EN-1-ONE DERIVATIVES

(75) Inventors: Jean-François Delhomel, Acq (FR); Karine Caumont-Bertrand, Frelinghien (FR)

(73) Assignee: GENFIT, Loos (FR)

( * ) Notice: Subject to any disclaimer, the term of this patent is extended or adjusted under 35 U.S.C. 154(b) by 63 days.

(21) Appl. No.: 10/563,057

(22) PCT Filed: Jul. 8, 2004

(86) PCT No.: PCT/FR2004/001797

§ 371 (c)(1),
(2), (4) Date: Feb. 2, 2006

(87) PCT Pub. No.: WO2005/005369

PCT Pub. Date: Jan. 20, 2005

(65) Prior Publication Data

US 2006/0142611 A1 Jun. 29, 2006

(30) Foreign Application Priority Data

Jul. 8, 2003 (FR) .................................. 03 08354

(51) Int. Cl.
*C07C 323/00* (2006.01)
*C07C 59/00* (2006.01)
*C07C 65/00* (2006.01)

(52) U.S. Cl. ..................... 562/431; 562/471; 562/472

(58) Field of Classification Search ..................... None
See application file for complete search history.

(56) References Cited

U.S. PATENT DOCUMENTS 4,656,305 A 4/1987 Vanstone et al.
5,523,302 A * 6/1996 Cain et al. ................ 514/254.1

FOREIGN PATENT DOCUMENTS

GB 1 469 845 4/1977

OTHER PUBLICATIONS

International Search Report for PCT/FR2004/001797 dated Nov. 22, 2004 (English and French).
Szajda et al., *New alkoxycarbonylalkyloxychalcones and their α, β-dibromo derivatives of potential antimicrobial activity*, Pharmazie, vol. 44, No. 3, Mar. 1989, pp. 190-191, XP002271328.
Database Caplus May 12, 1984, XP002271330, abstract of Palanowski et al., *Synthesis of potential vasoactive compounds, I. phenylacrylophenone derivatives*, ACTA Poloniae Pharmaceutica, vol. 24, No. 6, 1967, pp. 567-574, 2 pages.
Database Caplus May 12, 1984, XP002271332, abstract of Safak et al., *Chalcones, II. Synthesis of some chalcone derivatives and their antifungal activity against Candida albicans*, FABAD Farmasotik Bilimler Dergisi, vol. 8, No. 2, 1983, pp. 80-88, 1 page.
Database Caplus Feb. 19, 1994, XP002271333, abstract of Japanese patent No. 05-255655, Oct. 5, 1993, 2 pages.
European Patent Office, Patent Abstracts of Japan, abstract of JP 02-003670, Jan. 9, 1990, 1 page.

* cited by examiner

*Primary Examiner*—Paul A. Zucker
(74) *Attorney, Agent, or Firm*—Nixon & Vanderhye P.C.

(57) ABSTRACT

The invention relates to a method for the preparation of de 1,3-diphenylprop-2-en-1-one substituted on one of the two phenyl groups by a carboxyalkyloxy group or a carboxyalkylthio group.

15 Claims, No Drawings

PREPARATION OF 1,3-DIPHENYLPROP-2-EN-1-ONE DERIVATIVES

This application is the U.S. national phase of international application PCT/FR2004/001797 filed 8 Jul. 2004 which designated the U.S. and claims benefit of FR 03/08354 filed 8 Jul. 2003, the entire contents of each of which are hereby incorporated by reference.

The invention relates to a novel method for the preparation of 1,3-diphenylprop-2-en-1-one derivatives substituted on one of the two phenyl groups by a carboxyalkyloxy group or a carboxyalkylthio group.

Generally, 1,3-diphenylpropen-1-ones are prepared by a condensation reaction of an aldehyde with a ketone in a Claisen-Schmidt reaction (March J., 1992, "Advanced Organic Chemistry", Fourth Edition, 940, Wiley Interscience).

Classically, 1,3-diphenylprop-2-en-1-ones substituted by a carboxyalkyloxy group are obtained by said method from starting materials (aldehyde and ketone) which are selected in such a way as to be substituted by a carboxyalkyloxy group or by the corresponding ester. This sequence of steps may be summarized by one of the following reaction diagrams:

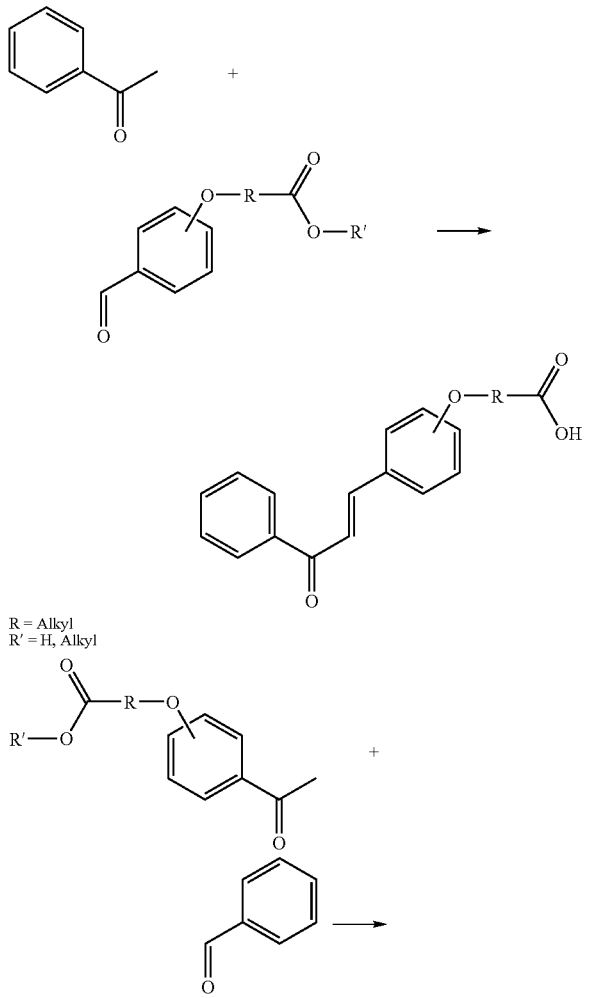

R = Alkyl
R' = H, Alkyl

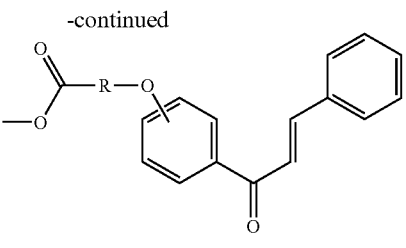

R = Alkyl
R' = H, Alkyl

However, the acidic nature of the compound so obtained and the frequent presence in the reaction medium of secondary products and unreacted starting materials make purification by recrystallization or silica gel chromatography difficult and result in a significant reduction in the yield.

Thus, the use of this synthetic strategy for preparing compounds cited as example 1 and example 3 herein has not made it possible to achieve overall yields greater than 10%.

The inventors have now developed a method which is simple to carry out whereby 1,3-diphenyl-2-en-1-ones substituted by a carboxyalkloxy group or a carboxyalkylthio group can be obtained with high yields. The method differs from the aforementioned synthesis in that the carboxyalkloxy or carboxyalkylthio group is introduced in the form of the tert-butyl or isopropyl ester by reaction with a 1,3-diphenyl-2-en-1-one derivative substituted by a hydroxyl or thiol group. The latter is generally obtained by a Claisen-Schmidt reaction.

One embodiment of the inventive method is based on the use of the acid-labile protective group of carboxylic acid, for example of the type tert-butyl or isopropyl. The inventors have shown that said group can be added and cleaved under conditions compatible with the chemical structure of diphenyl-1,3-prop-2-en-1-ones. They have put these advantages to use to develop a novel method of synthesis which is the object of the invention.

1,3-diphenylprop-2-en-1-ones substituted by a carboxyalkyloxy group or a carboxyalkylthio group which are obtained in this manner are of major interest in the pharmaceutical or cosmetics field. In fact, said compounds concurrently display PPAR activator, antioxidant and anti-inflammatory properties and, as such, have a high therapeutic or prophylactic potential and in particular can be used for the treatment or prevention of cerebrovascular diseases, cardiovascular diseases, syndrome X, restenosis, diabetes, obesity, hypertension, inflammatory disorders, cancers or neoplasms (benign or malignant tumors), neurodegenerative, dermatologic diseases and disorders related to oxidative stress, for the prevention or treatment of the effects of ageing in general and for example skin ageing, particularly in the field of cosmetics (appearance of wrinkles, etc.).

The invention is therefore directed at providing a method of preparation of 1,3-diphenylprop-2-en-1-one derivatives substituted on one of the two phenyl groups by a carboxyalkyloxy or carboxyalkylthio group which is easy to carry out and which gives high yields.

This objective and others are attained by the invention which in particular has as object a method for preparing 1,3-diphenylprop-2-en-1-one derivatives substituted by a carboxyalkyloxy or carboxyalkylthio group, comprising a step, hereinbelow called (i), of contacting at least one 1,3-diphenylprop-2-en-1-one derivative substituted on one of the phenyl groups by a hydroxyl or thiol group with at least one halogenated compound represented by general formula (II) below, in which Y represents a halogen atom, R is a C1-C24 alkyl chain (containing from 1 to 24 carbon atoms) and R' is an acid-labile protective group of the carboxylic acid.

Said step may be summarized by one of the following reaction diagrams:

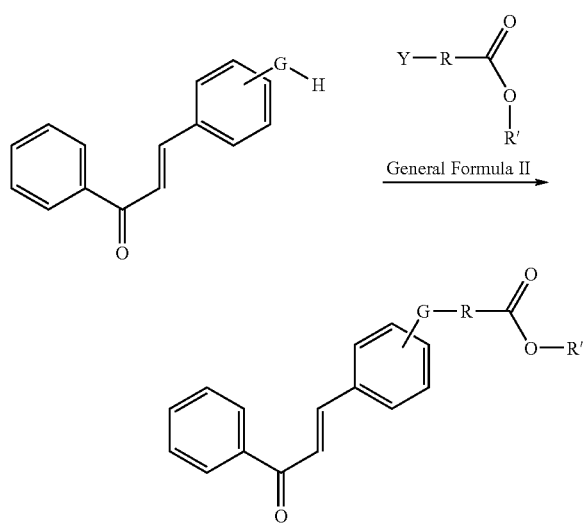

G = O or S,
R = alkyl chain, R' = acid-labile protective group
Step (i): first illustration

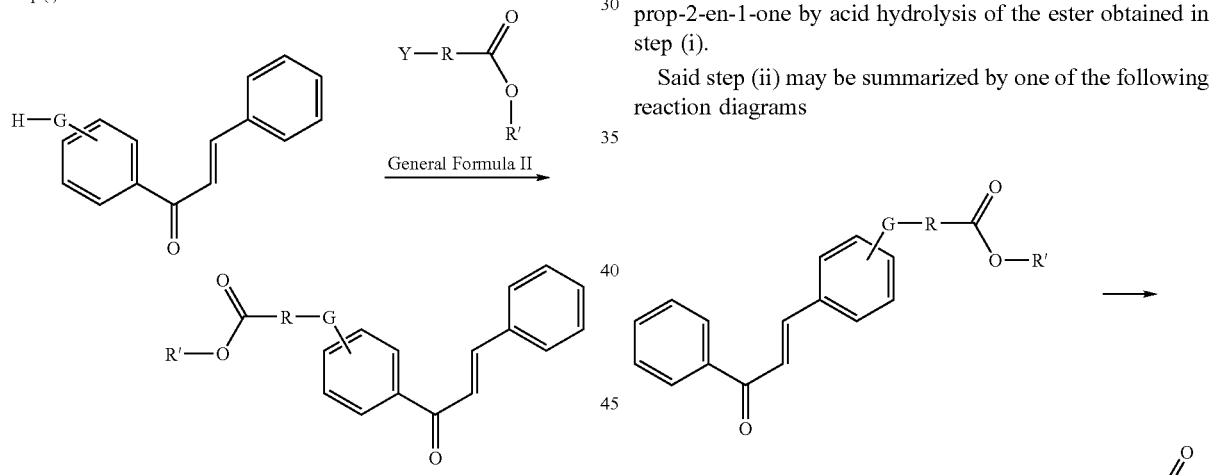

G = O or S,
R = alkyl chain, R' = acid-labile protective group
Step (i): second illustration Said step is advantageously carried out at a temperature comprised between 25 and 120° C. and more preferably between 80 and 120° C., preferably at atmospheric pressure, in the presence of a catalyst, such as cesium or potassium carbonate.

In a preferred manner, said step is repeated by several additions of the halogenated compound represented by general formula (II) and optionally the catalyst, such as cesium or potassium carbonate, advantageously until disappearance of the 1,3-diphenylprop-2-en-1-one derivative substituted on one of the phenyl groups by a hydroxyl or thiol group.

The alkyl chain R of the halogenated compound represented by general formula (II) designates a hydrocarbon chain, saturated or not, linear or cyclic containing from 1 to 24, preferably from 1 to 10 carbons and more particularly one carbon atom. Said chain can be substituted by one or more hydrocarbon groups, saturated, linear or cyclic containing from 1 to 12 carbon atoms, advantageously from 1 to 6 such as methyl, ethyl, propyl, isopropyl, butyl, isobutyl, pentyl, neopentyl, n-hexyl and more particularly methyl.

Preferably, the carboxylic acid protective group is selected in the group consisting of acid-labile functions of the type C1 to C5 alkyl (containing from 1 to 5 carbon atoms) substituted at the carbon atom linked to the carboxylic function by one or two linear or branched alkyl groups containing from 1 to 4 carbon atoms. More preferably, the protective group is selected from among tert-butyl and isopropyl groups.

In the present description, the terms "tert-butyl and isopropyl groups" are employed, but it must be understood that they can be generalized to any other protective group of carboxylic acid such as defined hereinabove.

Avantageously, the 1,3-diphenylprop-2-en-1-one derivative substituted by a hydroxyl or thiol group which is used in step (i) described hereinabove is obtained by a Claisen-Schmidt reaction in acidic or basic medium of a compound of the type acetophenone with a thio- or hydroxy-benzaldehyde derivative, or of a thio- or hydroxy-acetophenone derivative with a compound of the benzaldehyde type.

Subsequent to step (i) described hereinabove, the inventive method comprises a step (ii) of preparing the carboxyalkyloxy or carboxyalkylthio derivative of 1,3-diphenylprop-2-en-1-one by acid hydrolysis of the ester obtained in step (i).

Said step (ii) may be summarized by one of the following reaction diagrams

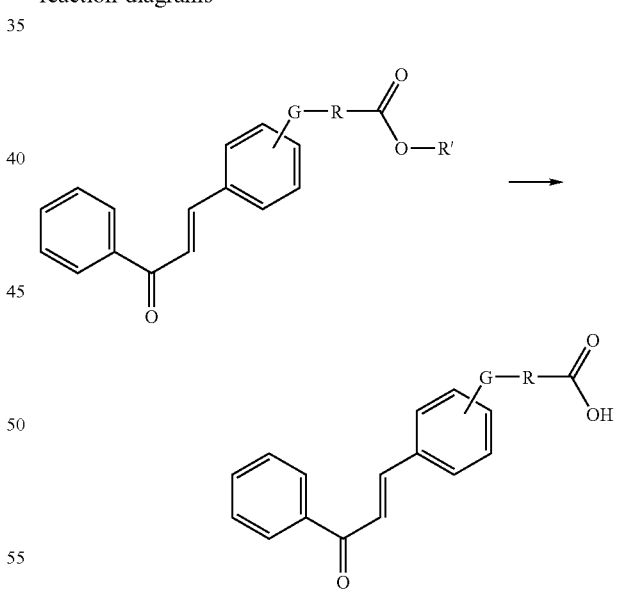

G = O or S,
R = alkyl chain and R' = protective group
Step (ii): first illustration

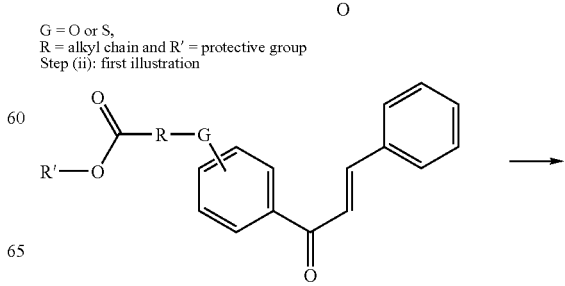

-continued

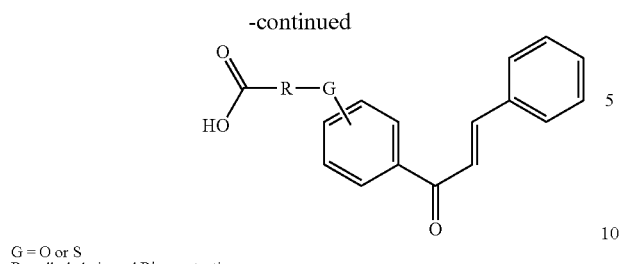

G = O or S
R = alkyl chain and R' = protective group
Step (ii): second illustration Advantageously, said acid hydrolysis step is carried out by contacting a 1,3-diphenylprop-2-en-1-one derivative substituted by an alkyloxycarbonylalkyloxy or alkyloxycarbonylalkylthio group with trifluoroacetic acid. Generally, the amount of trifluoroacetic acid is from 1 to 20 equivalents, and preferably from 8 to 12 equivalents. Advantageously, said step is carried out at a temperature of 0 to 100° C. and more preferably from 18 to 25° C., and preferably at atmospheric pressure.

More specifically, then, the invention describes the preparation of 1,3-diphenylprop-2-en-1-ones substituted by a carboxyalkyloxy group or a carboxyalkylthio group. The interest of said method lies in the combination of two synthetic steps : synthesis of tert-butyl or isopropyl esters (or any other protective group) from 1,3-diphenylprop-2-en-1-ones substituted on one of the phenyl groups by a hydroxyl or thiol group, followed by acid hydrolysis of the intermediate esters so prepared.

The tert-butyloxycarbonylalkyl or isopropyloxycarbonylalkyl group is added easily, with a high yield, by alkylation of a chemical precursor (hydroxy-1,3-diphenylprop-2-en-1-one or the sulfated analog of same) with a halogenated derivative. The tert-butyl or isopropyl ester intermediate so obtained can be easily purified, in particular by silica gel chromatography or by recrystallization.

The tert-butyl or isopropyl ester is cleaved to the corresponding acid by the action of trifluoroacetic acid. This method, adapted to the cleavage of the tert-butyl or isopropyl group, makes it possible to achieve complete conversion of the ester to the corresponding acid. The inventors have discovered that said method is compatible with the chemical structure of 1,3-diphenylprop-2-en-1-ones. Consequently, it does lead to the formation of degradation products and it allows production of the acids at higher yields than those classically observed.

The three steps that can be carried out in the scope of the invention may be summarized as follows.

First Step: Synthesis of the Chemical Precursor

The chemical precursor of the type hydroxy-1,3-diphenylprop-2-en-1-one or the sulfated analog of same can be prepared by the classical Claisen-Schmidt reaction in acidic or basic medium:

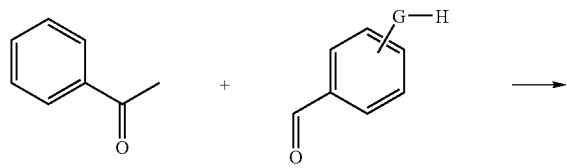

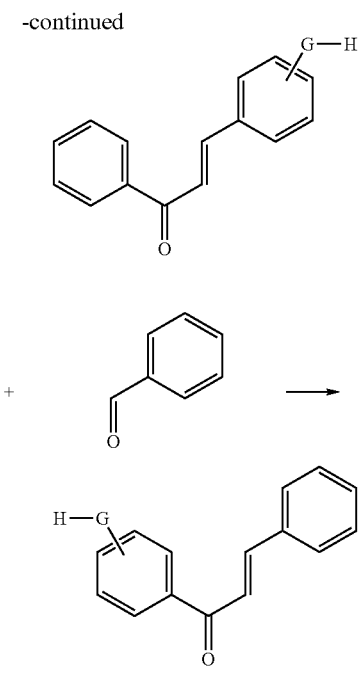

G = O or S

Compounds of the type acetophenone, hydroxy-acetophenone (or the sulfated analog of same), benzaldehyde and hydroxy-benzaldehyde (or the sulfated analog of same) used in said reaction can optionally be substituted by phenyl groups. Said substituents are selected more particularly in the group consisting of a halogen atom, an alkyl group, a thionitroso group, and an alkyloxy or alkylthio group.

The conditions in which to carry out said reaction in acidic or basic medium are familiar to those skilled in the art and can vary widely.

In an advantageous manner, said two compounds are contacted in stoichiometric proportions. Contact is preferably carried out at room temperature (between approximately 18° C. and 25° C.) and at atmospheric pressure.

In basic medium, the reaction is preferably carried out in the presence of a strong base, such as an alkaline metal hydroxide, like sodium hydroxide, or an alkaline metal alcoholate such as sodium ethylate.

In acidic medium, the reaction is preferably carried out in the presence of a strong acid, such as hydrochloric acid.

Advantageously, the synthesis in basic medium can be carried out in the following manner:

One molar-equivalent of the ketone and 1 molar-equivalent of the aldehyde are dissolved in a water-alcohol solution of sodium hydroxide at 20 molar equivalents. The mixture is stirred for 6 to 48 hours and preferably 16 to 20 hours at a temperature of 0 to 100° C. and preferably 18 to 25° C. The medium is then acidified (in particular to a pH of approximately 2), in particular with hydrochloric acid.

The expected hydroxy-1,3-diphenylprop-2-en-1-one (or the sulfated analog of same) can be obtained by precipitation or solid/liquid extraction after evaporation of the reaction medium. It can then be purified by silica gel chromatography or by recrystallization.

Advantageously, the synthesis in acidic medium can be carried out in the following manner:

One molar-equivalent of the ketone and 1 molar-equivalent of the aldehyde are dissolved in an ethanol solution saturated with gaseous hydrochloric acid. The mixture is stirred at a temperature of 0 to 100° C. and preferably at a temperature of 18 to 25° C. for 1 to 24 hours and preferably 1 to 6 hours, preferably at atmospheric pressure. The solvent is eliminated in particular by vacuum evaporation. The 1,3-diphenylprop-2-en-1-one is purified, in particular by chromatography on silica gel.

Second step: Preparation of the Tert-Butyl or Isopropyl Ester

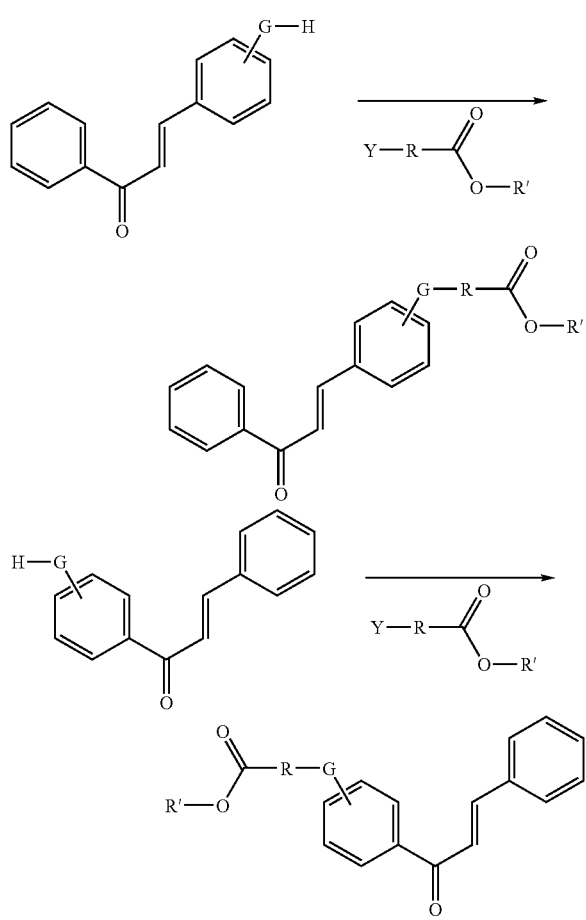

G representing an oxygen or sulfur atom,
Y representing a halogen atom,
R is an alkyl chain, preferably C1 to C6
R' = tert-butyl or isopropyl The reaction can be carried out in the following manner: One molar-equivalent of hydroxy-1,3-diphenylprop-2-en-1-one (or the sulfated analog of same) is dissolved in a solvent, preferably in acetonitrile or acetone, 1 to 10 equivalents and preferably 4 to 6 equivalents of cesium or potassium carbonate are added followed by addition of the derivative of type halogenated tert-butyl or isopropyl ester (1 to 20 molar-equivalents and preferably 4 to 8 molar-equivalents and even more preferably 6 equivalents). The mixture is heated with (vigorous) stirring at a temperature of 25 to 120° C. and preferably 100° C. for 1 to 24 hours and preferably 10 to 14 hours and even more preferably 10 hours, generally at atmospheric pressure. The solvent is eliminated, in particular by vacuum evaporation. The reaction medium is optionally reacted again with 3 to 6 molar-equivalents of the halogenated derivative and 3 to 5 molar-equivalents of cesium or potassium carbonate, said operation can be repeated until complete disappearance of the starting material.

The 1,3-diphenylprop-2-en-1-one substituted by a tert-butyloxycarbonylalkyloxy, tert-butyloxycarbonylalkylthio, isopropyloxycarbonylalkyloxy, or isopropyloxycarbonylalkylthio group is purified, in particular by silica gel chromatography.

Third Step: Preparation of the Acid from the Tert-Butyl or Isopropyl Ester

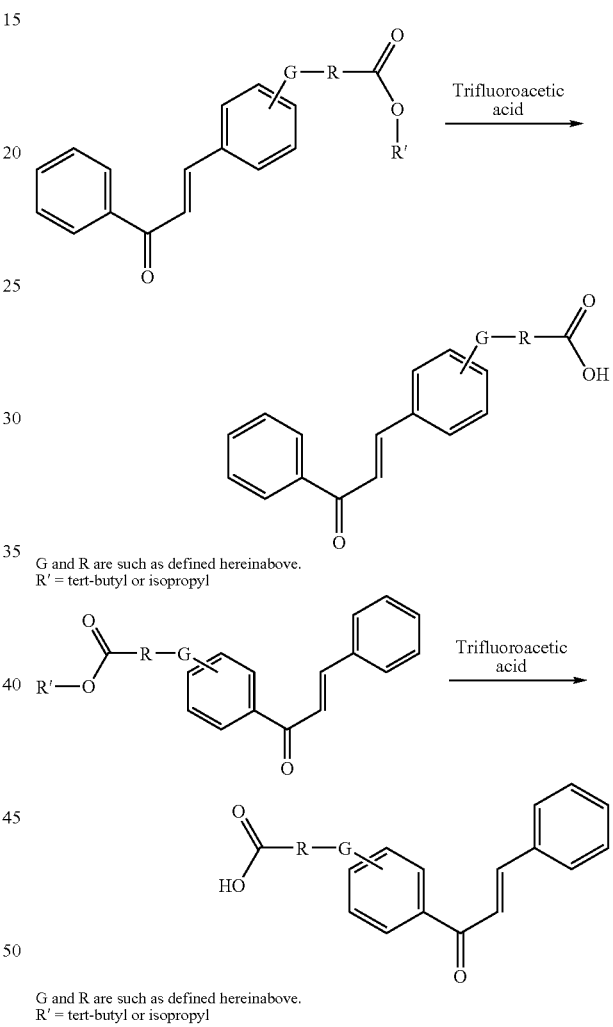

G and R are such as defined hereinabove.
R' = tert-butyl or isopropyl

One molar-equivalent of the 1,3-diphenylprop-2-en-1-one substituted by a tert-butyloxycarbonylalkyloxy group, by a tert-butyloxycarbonylalkylthio group, by an isopropyloxycarbonylalkyloxy group or by an isopropyloxycarbonylalkylthio group is dissolved in a solvent, such as dichloromethane. 1 to 20 equivalents and preferably 8 to 12 equivalents of acid and more preferably 10 equivalents of acid, preferably trifluoroacetic acid, are added. The mixture is stirred vigorously at a temperature of 0 to 100° C., preferably 18 to 25° C., for 1 to 24 hours and preferably 8 to 14 hours and more preferably 12 hours, preferably at atmospheric pressure. The solvent is eliminated, in particular by vacuum evaporation. The 1,3-diphenylprop-2-en-1- one substituted by a carboxyalkyloxy or carboxyalkylthio group is purified, in particular by silica gel chromatography. Preferably, the reaction is carried out at atmospheric pressure.

This method can advantageously be implemented for preparing compounds described in the French patent application FR 02 08571 filed by the Applicant on 8 Jul. 2002. Said compounds are represented by the general formula:

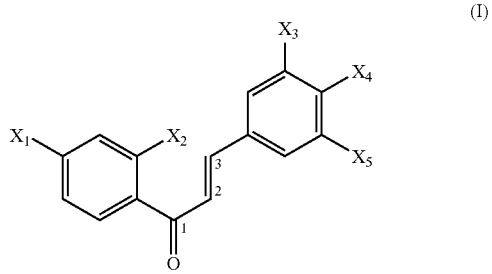

in which:
X1 represents a halogen or a -R1 group or a group corresponding to the following formula: -G1-R1;
X2 represents a hydrogen atom or a thionitroso group or an alkyloxy group or an alkylcarbonyloxy group or an alkylthio group or an alkylcarbonylthio group;
X3 represents a -R3 group or a group corresponding to the following formula: -G3-R3;
X4 represents a halogen or a thionitroso group or a -R4 group or a group corresponding to the following formula: -G4-R4;
X5 represents a -R5 group or a group corresponding to the following formula: -G5-R5;
R1, R3, R4, R5, which are the same or different, represent a hydrogen atom or an alkyl group substituted or not by a carboxylic acid function;
G1, G3, G4, G5, which are the same or different, represent an oxygen or sulfur atom;
with one of the groups X1, X3, X4 or X5 corresponding to the formula -G-R, in which R is an alkyl group containing a carboxylic acid function.

Advantageously, said synthetic method allows the preparation of compounds represented by general formula (I) in which none of the groups X1, X2, X3 and X4 is a hydroxyl or thiol group.

In a preferred manner, said method allows the preparation of compounds represented by general formula (I) for which at least one of the groups R3, R4 and R5 represents an alkyl group containing a carboxylic acid function.

In a preferred manner, R4 is an alkyl group containing a carboxylic acid function.

In a preferred manner, R4 is an alkyl group containing a carboxylic acid function and X3 and X5 are unsubstituted alkyls.

In a more preferred manner, X4 is a carboxydimethylmethyloxy or carboxydimethylmethylthio group.

In a preferred manner, G4 is an oxygen atom and R4 is an alkyl group containing a carboxylic acid function.

In a preferred manner, G4 is an oxygen atom and R4 is an alkyl group containing a carboxylic acid function and X3 and X5 are unsubstituted alkyls.

In a more preferred manner, X4 is a carboxydimethylmethyloxy group.

In a more preferred manner, X4 is a carboxydimethylmethylthio group.

Derivatives represented by general formula (I) such as described hereinabove can adopt the cis or trans conformation.

Advantageously, X3, X4 and X5 are not hydrogen atoms.

In the spirit of the invention, the term "alkyl" denotes a saturated hydrocarbon group, linear, branched or cyclic, halogenated or not, more particularly containing from 1 to 24, preferably 1 to 10, carbon atoms such as methyl, ethyl, propyl, isopropyl, butyl, isobutyl, tert-butyl, pentyl, neopentyl, n-hexyl. $C_1$-$C_2$ or $C_2$-$C_7$ groups are particularly preferred. Methyl and ethyl groups are more particularly preferred.

The term thionitroso refers to a nitroso group linked to the aromatic ring by means of a sulfur atom.

The term halogen represents a chlorine atom or a bromine atom or an iodine atom or a fluorine atom.

The term alkyloxy refers to an alkyl chain linked to the ring by means of an oxygen atom. The alkyl chain is defined hereinabove.

The term alkylthio refers to an alkyl chain linked to the ring by means of a sulfur atom (thioether bond). The alkyl chain is defined hereinabove.

The compounds or intermediate products (esters) preferably obtained by the inventive method are shown below with their corresponding formulas:

1-[4-chlorophenyl]-3-[3,5-dimethyl-4-tert-butyloxy-carbonyldimethylmethyloxyphenyl]prop-2-en-1-one

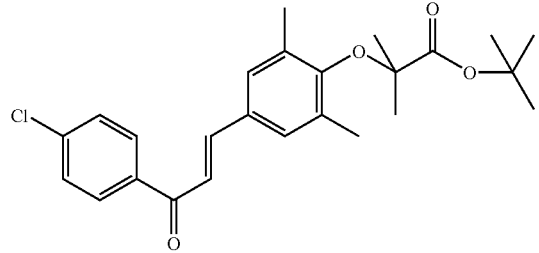

1-[4-chlorophenyl]-3-[3,5-dimethyl-4-isopropyloxy-carbonyldimethylmethyloxyphenyl]prop-2-en-1-one

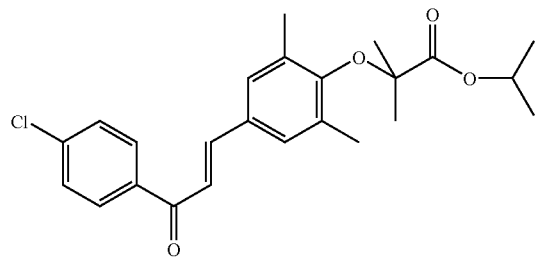

11
1-[4-chlorophenyl]-3-[3,5-dimethyl-4-carboxydimethylmethyloxyphenyl]prop-2-en-1-one

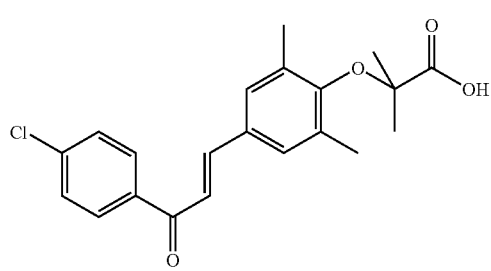

1-[4-methylthiophenyl]-3-[4-carboxydimethylmethyloxyphenyl]prop-2-en-1-one

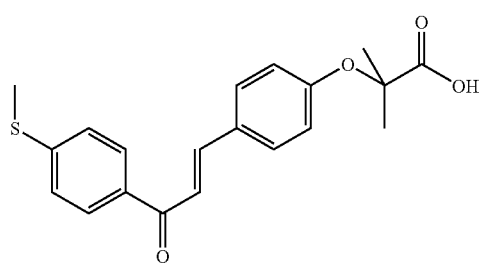

1-[4-carboxydimethylmethyloxyphenyl]-3-[4-chlorophenyl]prop-2-en-1-one

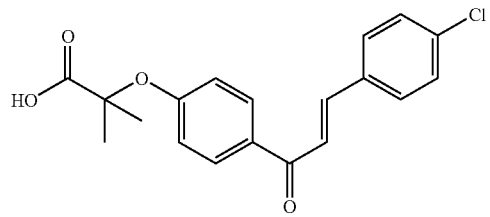

1-[4-carboxydimethylmethylthiophenyl]-3-[4-methylthiophenyl]prop-2-en-1-one

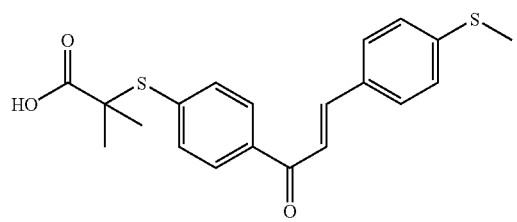

12
1-[4-carboxydimethylmethyloxyphenyl]-3-[4-methylthiophenyl]prop-2-en-1-one

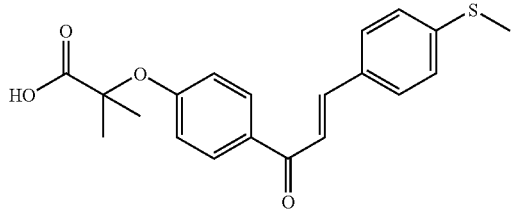

1-[4-methylthiophenyl]-3-[3,5-dimethyl-4-tert-butyloxycarbonyldimethylmethyloxyphenyl]prop-2-en-1-one

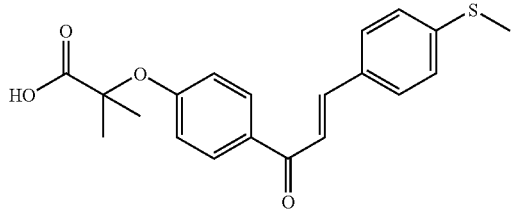

1-[4-methylthiophenyl]-3-[3,5-dimethyl-4-isopropyloxycarbonyldimethylmethyloxyphenyl]prop-2-en-1-one

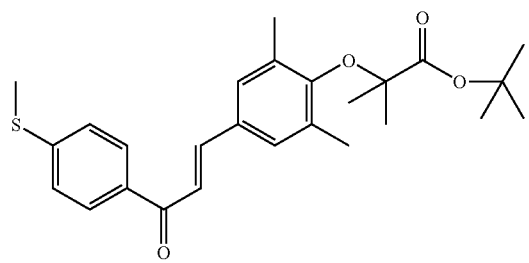

1-[4-methylthiophenyl]-3-[3,5-dimethyl-4-carboxydimethylmethyloxyphenyl]prop-2-en-1-one

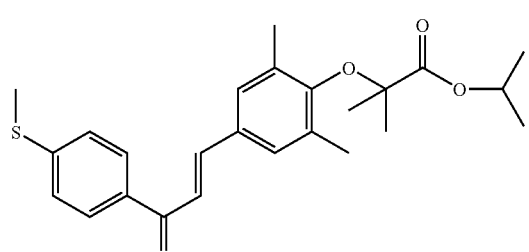

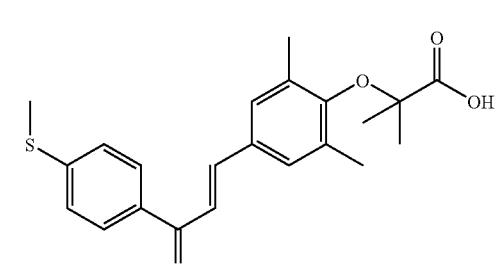

13
1-[2-methoxyphenyl]-3-[3,5-dimethyl-4-tert-buty-loxycarbonyldimethylmethyloxyphenyl]prop-2-en-1-one

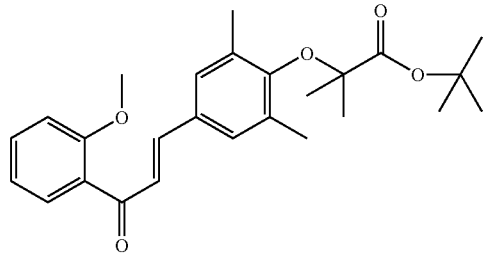

1-[2-methoxyphenyl]-3-[3,5-dimethyl-4-carboxy-dimethylmethyloxyphenyl]prop-2-en-1-one

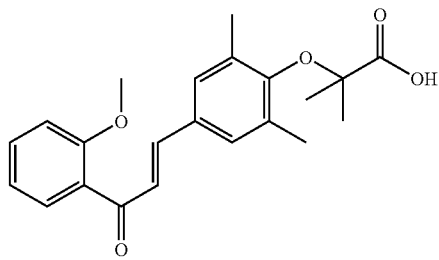

1-[4-hexyloxyphenyl]-3-[3,5-dimethyl-4-tert-buty-loxycarbonyldimethylmethyloxyphenyl]prop-2-en-1-one

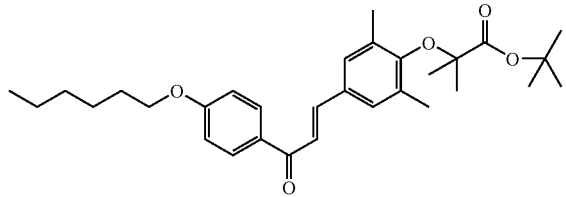

1-[4-hexyloxyphenyl]-3-[3,5-dimethyl-4-carboxy-dimethylmethyloxyphenyl]prop-2-en-1-one

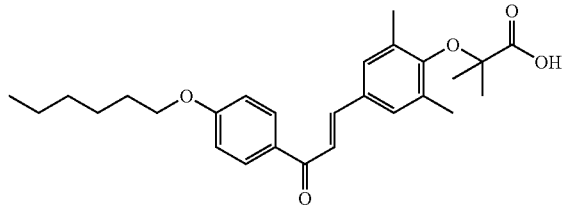

14
1-[2-methyloxy-4-chlorophenyl]-3-[3,5-dimethyl-4-tert-butyloxycarbonyldimethylmethyloxyphenyl]prop-2-en-1-one

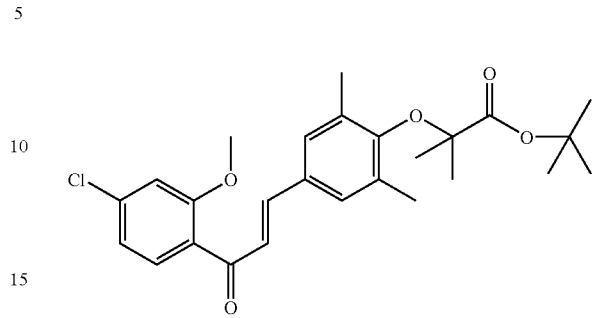

1-[2-methyloxy-4-chlorophenyl]-3-[3,5-dimethyl-4-carboxydimethylmethyloxyphenyl]prop-2-en-1-one

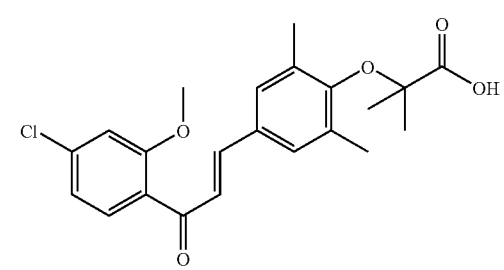

1-[4-heptylphenyl]-3-[3,5-dimethyl-4-tert-butyloxy-carbonyldimethylmethyloxyphenyl]prop-2-en-1-one

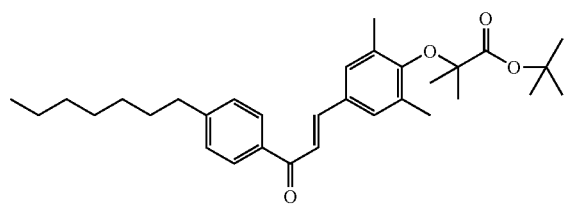

1-[4-heptylphenyl]-3-[3,5-dimethyl-4-carboxydim-ethylmethyloxyphenyl]prop-2-en-1-one

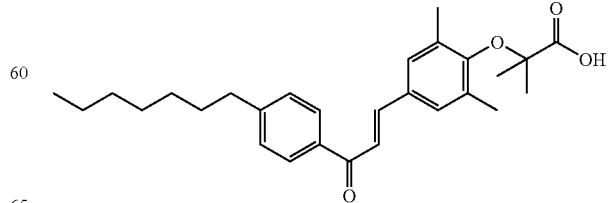

1-[4-bromophenyl]-3-[3,5-dimethyl-4-tert-butyloxy-carbonyldimethylmethyloxyphenyl]prop-2-en-1-one

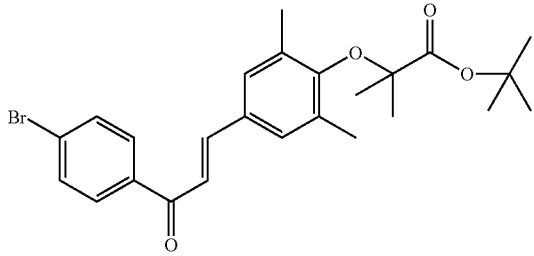

1-[4-bromophenyl]-3-[3,5-dimethyl-4-carboxy dimethylmethyloxyphenyl]prop-2-en-1-one

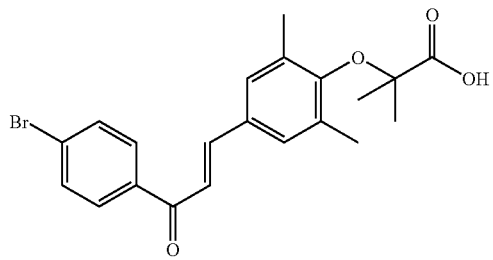

Other aspects and advantages of the invention will become apparent in the following examples, which are given for purposes of illustration and not by way of limitation.

EXAMPLES

1—Description of the General Synthetic Methods

General Method 1

Synthesis of hydroxy-1,3-diphenylprop-2-en-1-ones

One molar-equivalent of hydroxy-acetophenone (or the sulfated analog of same) and 1 molar-equivalent of aldehyde, or 1 molar-equivalent of hydroxy-benzaldehyde (or the sulfated analog of same) and 1 molar-equivalent of ketone are dissolved in an ethanol solution saturated with gaseous hydrochloric acid. The mixture is stirred at room temperature for 1 to 6 hours and the solvent is eliminated by vacuum evaporation. The hydroxy-1,3-diphenylprop-2-en-1-one is purified by silica gel chromatography or by recrystallization.

General Method 2

Alkylation of hydroxy-1,3-diphenylprop-2-en-1-ones

One molar-equivalent of hydroxy-1,3-diphenylpropen-1-one (or the sulfated analog of same) is dissolved in acetonitrile and 3 to 6 molar-equivalents of the halogenated derivative followed by 3 to 5 molar equivalents of potassium carbonate are added. The reaction medium is stirred vigorously under reflux for about 10 hours. The salts are eliminated by filtration.

Optionally, the reaction medium is reacted again with 3 to 6 molar-equivalents of the halogenated derivative and 3 to 5 molar-equivalents of potassium carbonate. This operation can be repeated until complete disappearance of the starting material.

Solvent and excess reagent are eliminated by vacuum evaporation and the expected product is purified by silica gel chromatography.

General Method 3

Acid hydrolysis of the tert-butyl esters of 1,3-diphenyl-prop-2-en-1-ones by trifluoroacetic acid:

One molar-equivalent of 1,3-diphenylprop-2-en-1-one tert-butyl ester is dissolved in dichloromethane, then 10 molar-equivalents of trifluoroacetic acid are added and the mixture is stirred at room temperature for 12 hours. The product which forms is purified by silica gel chromatography or by recrystallization.

2—Examples

Example 1

Synthesis of 1-[4-chlorophenyl]-3-[3,5-dimethyl-4-carboxydimethylmethyloxyphenyl]prop-2-en-1-one

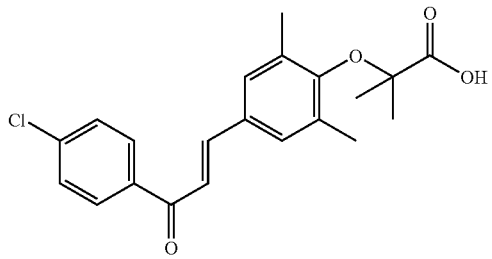

The method enabled the preparation of said compound with an overall yield of 56%.

Synthesis of the Chemical Precursor:

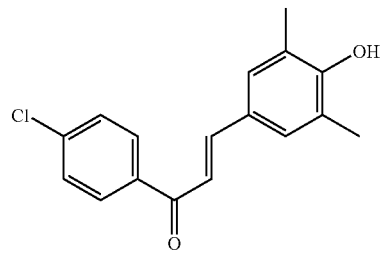

1-[4-chlorophenyl]-3-[3,5-dimethyl-4-hydroxyphenyl]prop-2-en-1-one (Compound 1)

This compound was synthesized from 4-chloroacetophenone and 3,5-dimethyl-4-hydroxybenzaldehyde according to general method 1 described hereinabove.

Purification was by silica gel chromatography (cyclohexane/ethyl acetate 95:5).

Yield: 91%

1H NMR CDCl$_3$ δ ppm: 2.30 (s, 6H), 7.32 (s, 2H), 7.34 (d, J=15.25 Hz, 1H), 7.47 (d, J=8.86 Hz, 2H), 7.75 (d, J=15.26 Hz, 1H), 7.97 (d, J=8.86 Hz, 2H).

Synthesis of the Tert-Butyl Ester:

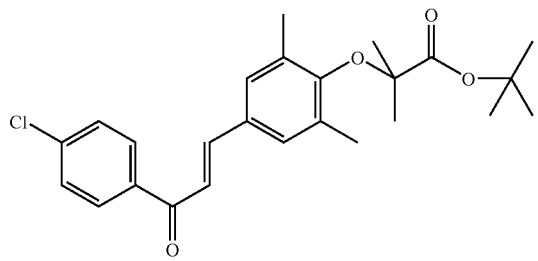

1-[4-chlorophenyl]-3-[3,5-dimethyl-4-tert-butyloxy-carbonyldimethylmethyloxyphenyl]prop-2-en-1-one (Compound 2)

This compound was synthesized from 1-[4-chlorophenyl]-3-[3,5-dimethyl-4-hydroxyphenyl]prop-2-en-1-one (Compound 1) and tert-butyl bromoisobutyrate according to general method 2 described hereinabove.

Purification was by silica gel chromatography (cyclohexane/ethyl acetate 90:10).

Yield: 70%

Acid Hydrolysis of the Tert-Butyl Ester:

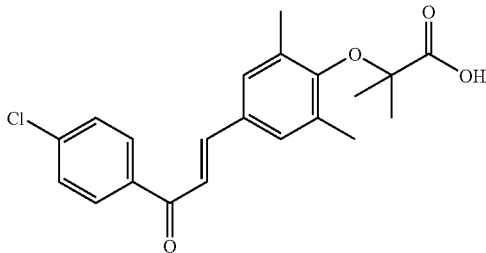

1-[4-chlorophenyl]-3-[3,5-dimethyl-4-carboxydimethylmethyloxyphenyl]prop-2-en-1-one (Compound 3)

This compound was synthesized from 1-[4-chlorophenyl]-3-[3,5-dimethyl-4-tert-butyloxycarbonyldimethylmethyloxyphenyl]prop-2-en-1-one (Compound 2) according to general method 3 described hereinabove.

Purification was by silica gel chromatography (dichloromethane/methanol 98:2).

Yield: 88%

1H NMR DMSO δ ppm: 1.39 (s, 6H), 2.22 (s, 6H), 7.58 (s, 2H), 7.67-7.62 (m, 3H), 7.82 (d, J=15.5 Hz, 1H), 8.17 (d, 2H), 12.96 (s, 1H) MS (Maldi-Tof): 373.3 (M+1)

Example 2

Synthesis of 1-[2-methoxyl-3-[3,5-dimethyl-4-carboxydimethylmethyloxyphenyl]prop-2-en-1-one

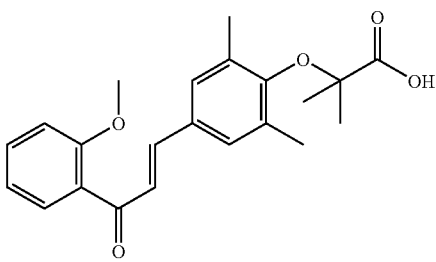

The method enabled the preparation of said compound with an overall yield of 20%.

Synthesis of the Chemical Precursor:

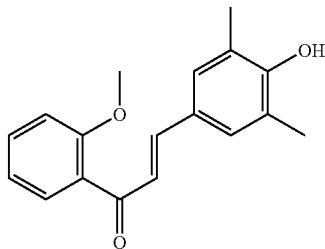

1-[2-methoxyphenyl]-3-[3,5-dimethyl-4-hydroxyphenyl]prop-2-en-1-one (Compound 4)

This compound was synthesized from 2-methoxyacetophenone and 3,5-dimethyl-4-hydroxybenzaldehyde according to general method 1 described hereinabove.

Purification was by silica gel chromatography (cyclohexane/ethyl acetate 80:20).

Yield: 66%

1H NMR CDCl3 δ ppm: 2.27 (s, 6H), 3.87 (s, 3H), 6.97-7.05 (m, 2H), 7.19 (d, 1H, J=15.96 Hz), 7.22 (s, 2H), 7.44 (m, 1H), 7.51 (d, 1H, J=15.48 Hz), 7.56 (dd, 1H, J=1.86 Hz, J=7.5 Hz)

Synthesis of the Tert-Butyl Ester:

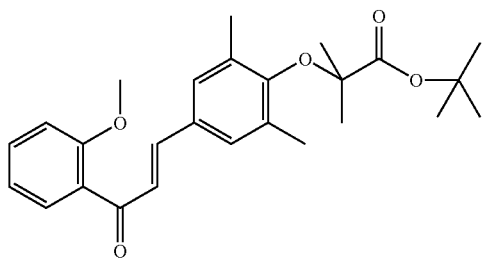

1-[2-methoxyphenyl]-3-[3,5-dimethyl-4-tert-butyloxycarbonyldimethylmethyloxyphenyl]prop-2-en-1-one (Compound 5)

This compound was synthesized from 1-[2-methoxyphenyl]-3-[3,5-dimethyl-4-hydroxyphenyl]prop-2-en-1-one (Compound 4) and tert-butyl bromoisobutyrate according to general method 2 described hereinabove.

Purification was by silica gel chromatography (cyclohexane/ethyl acetate 80:20).

Yield: 41%

Acid Hydrolysis of the Tert-Butyl Ester:

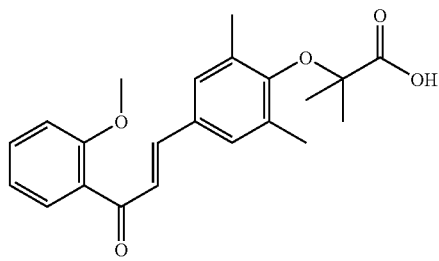

1-[2-methoxyphenyl]-3-[3,5-dimethyl-4-carboxydimethylmethyloxyphenyl]prop-2-en-1-one (Compound 6)

This compound was synthesized from 1-[2-methoxyphenyl]-3-[3,5-dimethyl-4-tert-butyloxycarbonyldimethylmethyloxyphenyl]prop-2-en-1-one (Compound 5) according to general method 3 described hereinabove.

Purification was by silica gel chromatography (dichloromethane/methanol 98:2).

Yield: 70%

1H NMR DMSO δ ppm: 1.38 (s, 6H), 2.19 (s, 6H), 3.93 (s, 3H), 7.05 (m, 1H), 7.20 (d, J=8.31 Hz, 1H), 7.25 (d, J=15.5 Hz, 1H), 7.37 (d, J=15.5 Hz, 1H), 7.39 (s, 2H), 7.46 (d, J=7.2 Hz, 1 H), 7.53 (m, 1H), 12.93 (s, 1H) MS (ES-MS): 367.1 (M−1)

Example 3

Synthesis of Ia 1-[4-methylthiophenyl]-3-[3,5-dimethyl-4-carboxydimethylmethyloxyphenyl]prop-2-en-1-one

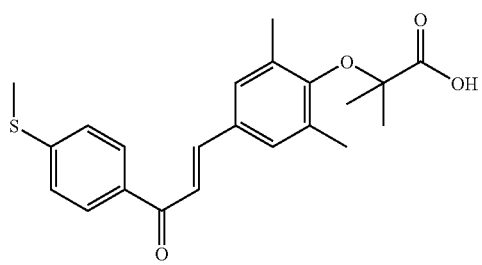

The method enabled the preparation of said compound with an overall yield of 49%.

Synthesis of the Chemical Precursor:

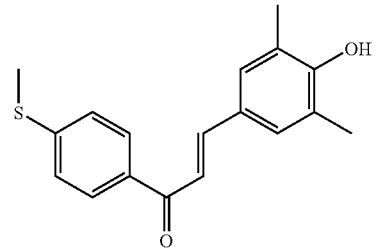

1-[4-methylthiophenyl]-3-[3,5-dimethyl-4-hydroxyphenyl]prop-2-en-1-one (Compound 7)

This compound was synthesized from 4-methylthioacetophenone and 3,5-dimethyl-4-hydroxybenzaldehyde according to general method 1 described hereinabove.

Purification was by silica gel chromatography (cyclohexane/ethyl acetate 80:20).

Yield: 86%

1H NMR DMSO δ ppm: 1.22 (s, 6H), 2.54 (s, 3H), 7.36 (d, J=8.20 Hz, 2H), 7.48 (s, 2H), 7.62 (d, J=15.7 Hz, 1H), 7.74 (d, J=15.7 Hz, 1H), 8.10 (d, J=8.20 Hz 2H), 8.92 (s, 1H)

Synthesis of the Tert-Butyl Ester:

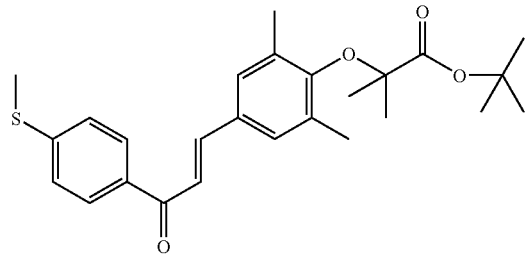

1-[4-methylthiophenyl]-3-[3,5-dimethyl-4-tert-butyloxycarbonyldimethylmethyloxyphenyl]prop-2-en-1-one (Compound 8)

This compound was synthesized from 1-[4-methylthiophenyl]-3-[3,5-dimethyl-4-hydroxyphenyl]prop-2-en-1-one (Compound 7) and tert-butyl bromoisobutyrate. 1-[4-methylthiophenyl]-3-[3,5-dimethyl-4-hydroxyphenyl]prop-2-en-1-one was dissolved in acetonitrile and 3 molar-equivalents of potassium carbonate and 3 molar-equivalents of tert-butyl bromoisobutyrate were then added. The mixture was stirred at 80° C. for 12 hours, then brought to room temperature. The salts were eliminated by filtration. Three molar-equivalents of potassium carbonate and 3 molar-equivalents of tert-butyl bromoisobutyrate were added. The mixture was reacted for another 12 hours, then brought to room temperature. The salts were eliminated by filtration. Three molar-equivalents of potassium carbonate and 3 molar-equivalents of tert-butyl bromoisobutyrate were added. The mixture was stirred at 80° C. for 12 hours and the salts were eliminated by filtration. The solvents were eliminated by vacuum evaporation. Purification was by silica gel chromatography (cyclohexane/ethyl acetate 90:10).
Yield: 74%

Acid Hydrolysis of the Tert-Butyl Ester:

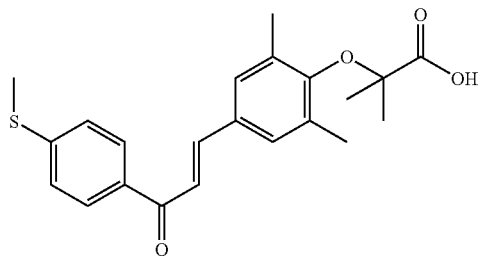

1-[4-methylthiophenyl]-3-[3,5-dimethyl-4-carboxy-dimethylmethyloxyphenyl]prop-2-en-1-one (Compound 9)

This compound was synthesized from 1-[4-methylthiophenyl]-3-[3,5-dimethyl-4-tert-butyloxycarbonyldimethylmethyloxyphenyl]prop-2-en-1-one (Compound 8) according to general method 3 described hereinabove.

Purification was by silica gel chromatography (dichloromethane/methanol 98:2)
Yield: 81%

1H NMR DMSO δ ppm: 1.39 (s, 6H), 2.22 (s, 6H), 2.57 (s, 3H), 7.40 (d, J=8.55 Hz, 2H), 7.57 (s, 2H), 7.62 (d, J=15.5 Hz, 1H), 7.83 (d, J=15.5 Hz, 1H) 8.10 (d, J=8.55 Hz, 2H), 12.97 (s, 1H) MS (ES-MS): 383.3 (M−1)

Example 4

Synthesis of 1-[4-hexyloxyphenyl]-3-[3,5-dimethyl-4-carboxydimethylmethyloxyphenyl]prop-2-en-1-one

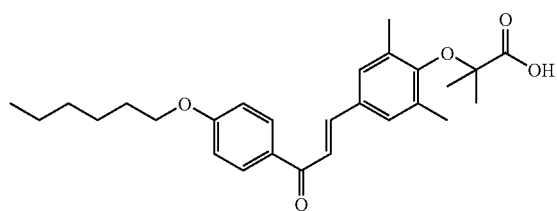

The method enabled the preparation of said compound with an overall yield of 24%.

Synthesis of the Chemical Precursor:

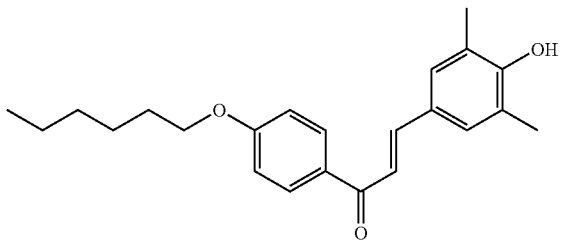

1-[4-hexyloxyphenyl]-3-[3,5-dimethyl-4-hydroxyphenyl]prop-2-en-1-one (Compound 10)

This compound was synthesized from 4-hexyloxyacetophenone and 3,5-dimethyl-4-hydroxybenzaldehyde according to general method 1 described hereinabove. The product crystallized at the end of the reaction and was dried.
Yield: 63%

1H NMR DMSO δ ppm: 0.88 (m, 3H), 1.28-1.43 (m, 6H), 1.72 (m, 2H), 2.21 (s, 6H), 4.05 (t, J=6.42 Hz, 2H), 7.40 (d, J=8.43 Hz, 2H), 7.48 (s, 2H), 7.57 (d, J=15.24 Hz, 1H), 7.72 (d, J=15.24 Hz, 1H), 8.12 (d, J=8.43 Hz, 2H), 8.89 (s, 1H)

Synthesis of the Tert-Butyl Ester:

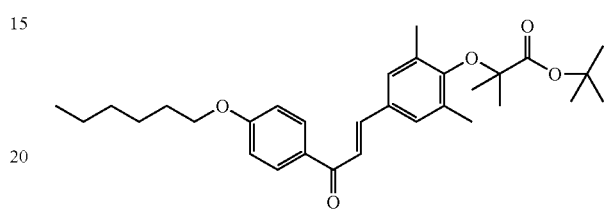

1-[4-hexyloxyphenyl]-3-[3,5-dimethyl-4-tert-butyloxycarbonyldimethylmethyloxyphenyl]prop-2-en-1-one (Compound 11)

This compound was synthesized from 1-[4-hexyloxyphenyl]-3-[3,5-dimethyl-4-hydroxyphenyl]prop-2-en-1-one (Compound 10) and tert-butyl bromoisobutyrate according to general method 2 described hereinabove.

Purification was by silica gel chromatography (cyclohexane/ethyl acetate 95:5).
Yield: 75%

Acid Hydrolysis of the Tert-Butyl Ester:

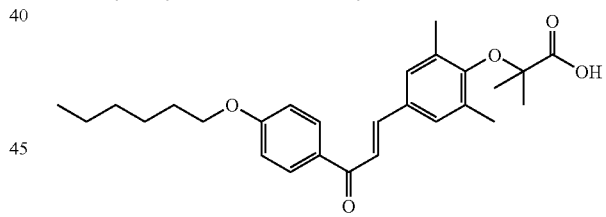

1-[4-hexyloxyphenyl]-3-[3,5-dimethyl-4-carboxydimethylmethyloxyphenyl]prop-2-en-1-one (Compound 12)

This compound was synthesized from 1-[4-hexyloxyphenyl]-3-[3,5-dimethyl-4-ter-butyloxycarbonyldimethylmethyloxyphenyl]prop-2-en-1-one (Compound 11) according to general method 3 described hereinabove.

Purification was by recrystallization in methanol. Yield: 51%

1H NMR DMSO δ ppm: 0.88 (t, J=6.33 Hz, 3H), 1.30 (m, 4H), 1.39 (s, 6H), 1.44 (m, 2H), 1.73 (m, 2H), 2.22 (s, 6H), 4.06 (t, J=6.30 Hz, 2H), 7.06 (d, J=8.61 Hz, 2H), 7.56 (s, 2H), 7.58 (d, J=15.5 Hz, 1H), 7.82 (d, J=15.5 Hz, 1H), 8.13 (d, J=6.61 Hz, 2H) MS (ES-MS): 437.2 (M−1)

Example 5

Synthesis of 1-[2-methyloxy-4-chlorophenyl]-3-[3,5-dimethyl-4-carboxydimethylmethyloxyphenyl]prop-2-en-1-one

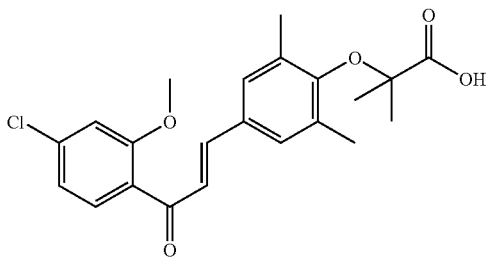

The method enabled the preparation of said compound with an overall yield of 22%.

Synthesis of the Chemical Precursor:

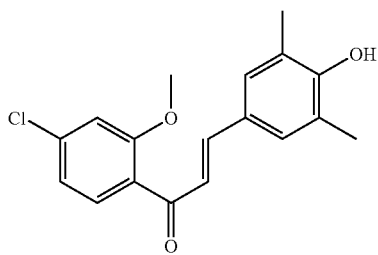

1-[2-methyloxy-4-chlorophenyl]-3-[3,5-dimethyl-4-hydroxyphenyl]prop-2-en-1-one (Compound 13)

This compound was synthesized from 4-chloro-2-methoxyacetophenone and 3,5-dimethyl-4-hydroxybenzaldehyde according to general method 1 described hereinabove.

Purification was by silica gel chromatography (cyclohexane/ethyl acetate 85:15).

Yield: 72%

1H NMR DMSO δ ppm: 2.21 (s, 6H), 3.90 (s, 3H), 7.12 (m, 1H), 7.23 (d, J=15.5 Hz, 1 H), 7.29 (d, J=1.80 Hz, 1H), 7.38 (d, J=15.5 Hz, 1 H), 7.41 (s, 2H), 7.48 (d, J=7.98 Hz, 1H)

Synthesis of the Tert-Butyl Ester:

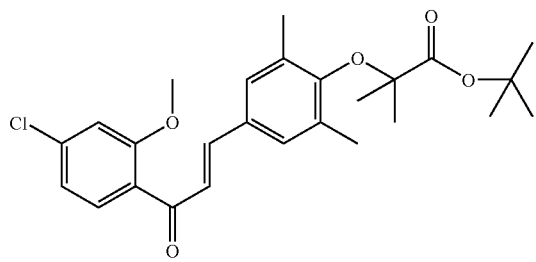

1-[2-methyloxy-4-chlorophenyl]-3-[3,5-dimethyl-4-tert-butyloxycarbonyldimethylmethyloxyphenyl]prop-2-en-1-one (Compound 14)

This compound was synthesized from 1-[2-methyloxy-4-chlorophenyl]-3-[3,5-dimethyl-4-hydroxydimethylmethyloxyphenyl]prop-2-en-1-one (Compound 13) and tert-butyl bromoisobutyrate according to general method 2 described hereinabove. Purification was by silica gel chromatography (cyclohexane/ethyl acetate 90:10).

Yield: 43%

Acid Hydrolysis of the Tert-Butyl Ester:

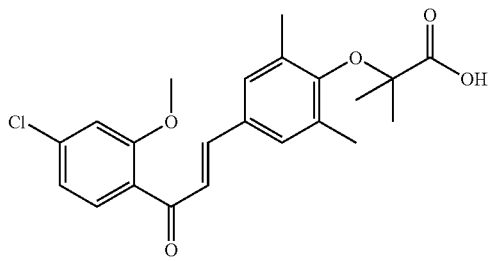

1-[2-methyloxy-4-chlorophenyl]-3-[3,5-dimethyl-4-carboxydimethylmethyloxyphenyl]prop-2-en-1-one (Compound 15)

This compound was synthesized from 1-[2-methoxy-4-chlorophenyl]-3-[3,5-dimethyl-4-tert-butyloxycarbonyldimethylmethyloxyphenyl]prop-2-en-1-one (Compound 14) according to general method 3 described hereinabove. Purification was by silica gel chromatography (dichloromethane/methanol 98:2).

Yield: 70%

1H NMR DMSO δ ppm: 1.38 (s, 6H), 2.19 (s, 6H), 3.89 (s, 3H), 7.12 (dd, J=7.98, J=1.71 Hz, 1H), 7.23 (d, J=15.56 Hz, 1H), 7.29 (d, J=1.71 Hz, 1H), 7.38 (d, J=15.7 Hz, 1H), 7.41 (s, 2H), 7.48 (d, J=7.98 Hz, 1H) MS (ES-MS): 401.2 (M−1)

Example 6

Synthesis of 1-[4-bromophenyl]-3-[3,5-dimethyl-4-carboxydimethylmethyloxyphenyl]prop-2-en-1-one

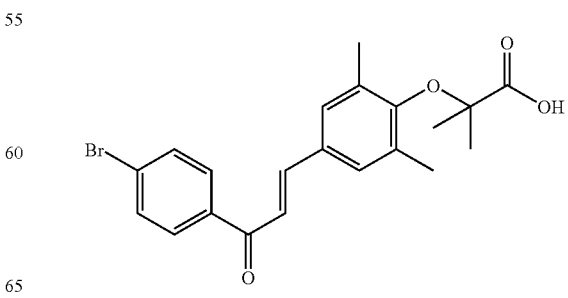

The method enabled the preparation of said compound with an overall yield of 21%.

Synthesis of the Chemical Precursor:

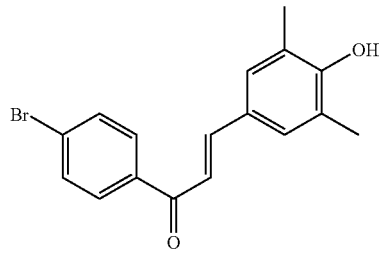

1-[4-bromophenyl]-3-[3,5-dimethyl-4-hydroxyphenyl]prop-2-en-1-one (Compound 16)

This compound was synthesized from 4-bromoacetophenone and 3,5-dimethyl-4-hydroxybenzaldehyde according to general method 1 described hereinabove. Purification was by silica gel chromatography (cyclohexane/ethyl acetate 90:10).

Yield: 37%

1H NMR DMSO δ ppm: 2.30 (s, 6H), 7.32 (s, 2H), 7.56-7.66 (m, 3H), 7.75 (d, J=15.27 Hz, 1H), 7.90 (d, J=8.70 Hz, 2H), 9.82 (s, 1H)

Synthesis of the Tert-Butyl Ester:

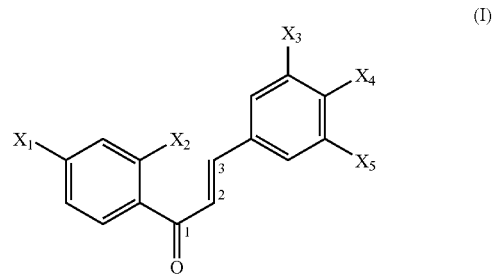

1-[4-bromophenyl]-3-[3,5-dimethyl-4-tert-butyloxycarbonyldimethylmethyloxyphenyl]prop-2-en-1-one (Compound 17)

This compound was synthesized from 1-[4-bromophenyl]-3-[3,5-dimethyl-4-hydroxyphenyl]prop-2-en-1-one (Compound 16) and tert-butyl bromoisobutyrate according to general method 2 described hereinabove. Purification was by silica gel chromatography (cyclohexane/ethyl acetate 90:10).

Yield: 75%

Acid Hydrolysis of the Tert-Butyl Ester:

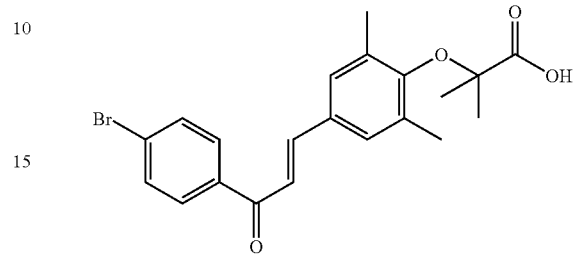

1-[4-bromophenyl]-3-[3,5-dimethyl-4-carboxydimethylmethyloxyphenyl]prop-2-en-1-one (Compound 18)

This compound was synthesized from 1-[4-bromophenyl]-3-[3,5-dimethyl-4-tert-butyloxycarbonyldimethylmethyloxyphenyl]prop-2-en-1-one (Compound 17) according to general method 3 described hereinabove. Purification was by silica gel chromatography (dichloromethane/methanol 98:2).

Yield: 38%

$^1$H NMR DMSO δ ppm: 1.39 (s, 6H), 2.22 (s, 6H), 7.58 (s, 2H), 7.65 (d, J=15.39 Hz, 1H), 7.84-7.77 (m, 3H), 8.09 (d, J=8.19 Hz, 2H), 13.01 (s, 1H)

MS (ES-MS): 417.2 (M−1)

The invention claimed is:

1. A method for preparing 1,3-diphenylprop-2-en-1-one derivatives substituted by a carboxyalkyloxy or carboxyalkylthio group of the following formula:

(I)

in which:
X1 represents a halogen or a -R1 group or a group corresponding to the following formula: -G1-R1;
X2 represents a hydrogen atom or a thionitroso group or an alkyloxy group or an alkylcarbonyloxy group or an alkylthio group or an alkylcarbonylthio group;
X3 represents a -R3 group or a group corresponding to the following formula: -G3-R3;
X4 represents a halogen or a thionitroso group or a -R4 group or a group corresponding to the following formula: -G4-R4;
X5 represents a -R5 group or a group corresponding to the following formula: -G5-R5;

R1, R3, R4, R5, which are the same or different, represent a hydrogen atom or an alkyl group substituted or not by a carboxylic acid function;

G1, G3, G4, G5, which are the same or different, represent an oxygen or sulfur atom;

with one of the groups X1, X3, X4 or X5 corresponding to the formula -G-R, in which R is an alkyl group containing a carboxylic acid function, weherein said method comprises the following steps:

(i) contacting at least one 1,3-diphenylprop-2-en-1-one derivative substituted on one of the two phenyl groups by a hydroxyl or thiol group with at least one halogenated compound represented by general formula (II):

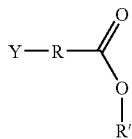

in which Y represents a halogen atom, R is a C1-C24 alkyl chain and R' is an acid-labile protective group of carboxylic acid;

(ii) acid hydrolysis of the ester obtained in step (i).

2. The method according to claim 1, wherein the carboxylic acid protective group of the compound represented by formula (II) is selected from acid-labile groups of the C1 to C5 alkyl type substituted at the carbon atom linked to the carboxylic function by one or two linear or branched alkyl groups containing from 1 to 4 carbon atoms.

3. The method according to claim 1, wherein the carboxylic acid protective group of the compound represented by formula (II) is selected from tert-butyl and isopropyl groups.

4. The method according to claim 1, wherein R is a C1-C10 alkyl chain, optionally substituted by one or more hydrocarbon groups, saturated, linear or cyclic containing from 1 to 12 carbon atoms.

5. The method according to claim 1, wherein step (i) is carried out at a temperature comprised between 25 and 120° C.

6. The method according to claim 1, wherein step (i) is carried out in the presence of a catalyst.

7. The method according to claim 1, wherein step (i) is carried out in the presence of cesium or potassium carbonate as catalyst.

8. The method according to claim 1, wherein step (i) is repeated by several additions of the halogenated compound represented by general formula (II) and if necessary of the catalyst.

9. The method according to claim 1, wherein 1,3-diphenylprop-2-en-1-one derivative substituted by a hydroxyl or thiol group, which is used in step (i) is obtained by a Claisen-Schmidt reaction in acidic or basic medium of a compound of the type acetophenone with a thio- or hydroxy-benzaldehyde derivative, or of a thio- or hydroxy-acetophenone derivative with a compound of the benzaldehyde type.

10. The method according to claim 1, wherein acid hydrolysis step (ii) is carried out by contacting a 1,3-diphenylprop-2-en-1-one derivative substituted by an alkyloxycarbonylalkyloxy or alkyloxycarbonylalkylthio group with trifluoroacetic acid.

11. The method according to claim 1, wherein acid hydrolysis step (ii) is carried out by contacting a 1,3-diphenylprop-2-en-1-one derivative substituted by an alkyloxycarbonylalkyloxy or alkyloxycarbonylalkylthio group with trifluoroacetic acid in an amount from 1 to 20 equivalents.

12. The method according to claim 1, wherein step (ii) is carried out at a temperature of 0 to 100° C.

13. The method according to claim 5, wherein step (i) is carried out at a temperature comprised between 80 and 120° C.

14. The method according to claim 11, wherein acid hydrolysis step (ii) is carried out by contacting a 1,3-diphenylprop-2-en-1-one derivative substituted by an alkyloxycarbonylalkyloxy or alkyloxycarbonylalkylthio group with trifluoroacetic acid in an amount from 8 to 12 equivalents.

15. The method according to claim 12, wherein step (ii) is carried out at a temperature of 18 to 25° C.

* * * * *